United States Patent
Ren et al.

(10) Patent No.: US 11,225,531 B2
(45) Date of Patent: Jan. 18, 2022

(54) GLYCOSAMINOGLYCAN DERIVATIVE AND PREPARATION METHOD THEREFOR AND USE THEREOF

(71) Applicant: SHENZHEN HEPALINK PHARMACEUTICAL GROUP CO., LTD., Guangdong (CN)

(72) Inventors: Lige Ren, Guangdong (CN); Jingwen Wang, Guangdong (CN); Xuewen Jin, Guangdong (CN); Lili Zhang, Guangdong (CN); Senmao Lin, Guangdong (CN); Li Li, Guangdong (CN)

(73) Assignee: SHENZHEN HEPALINK PHARMACEUTICAL GROUP CO., LTD., Guangdong (CN)

( * ) Notice: Subject to any disclaimer, the term of this patent is extended or adjusted under 35 U.S.C. 154(b) by 0 days.

(21) Appl. No.: 16/966,951

(22) PCT Filed: Jan. 29, 2019

(86) PCT No.: PCT/CN2019/073572
§ 371 (c)(1),
(2) Date: Aug. 3, 2020

(87) PCT Pub. No.: WO2019/149179
PCT Pub. Date: Aug. 8, 2019

(65) Prior Publication Data
US 2021/0032376 A1 Feb. 4, 2021

(30) Foreign Application Priority Data
Feb. 2, 2018 (CN) .......................... 201810105528.3

(51) Int. Cl.
C08B 37/00 (2006.01)
A61P 35/04 (2006.01)
A61K 31/737 (2006.01)

(52) U.S. Cl.
CPC ........ *C08B 37/0063* (2013.01); *A61K 31/737* (2013.01); *A61P 35/04* (2018.01)

(58) Field of Classification Search
None
See application file for complete search history.

(56) References Cited

U.S. PATENT DOCUMENTS

| | | |
|---|---|---|
| 2005/0137167 A1 | 6/2005 | Casu et al. |
| 2005/0222084 A1 | 10/2005 | Casu et al. |
| 2016/0237178 A1 | 8/2016 | Torri et al. |
| 2016/0297896 A1 | 10/2016 | Torri et al. |

FOREIGN PATENT DOCUMENTS

| | | |
|---|---|---|
| CN | 1396930 A | 2/2003 |
| CN | 1547477 A | 11/2004 |
| CN | 105504097 A | 4/2016 |
| CN | 105744940 A | 7/2016 |
| CN | 105814086 A | 7/2016 |

OTHER PUBLICATIONS

International Search Report for PCT/CN2019/073572 dated Apr. 28, 2019.
English Abstract for CN-105504097, Publication Date: Apr. 20, 2016.

*Primary Examiner* — Layla D Berry
(74) *Attorney, Agent, or Firm* — Millen White Zelano & Branigan, PC; Brion P. Heaney

(57) ABSTRACT

Disclosed are a carboxylated glycosaminoglycan derivative, a preparation method therefor, and the use thereof for inhibiting tumor growth and/or metastasis.

17 Claims, 1 Drawing Sheet

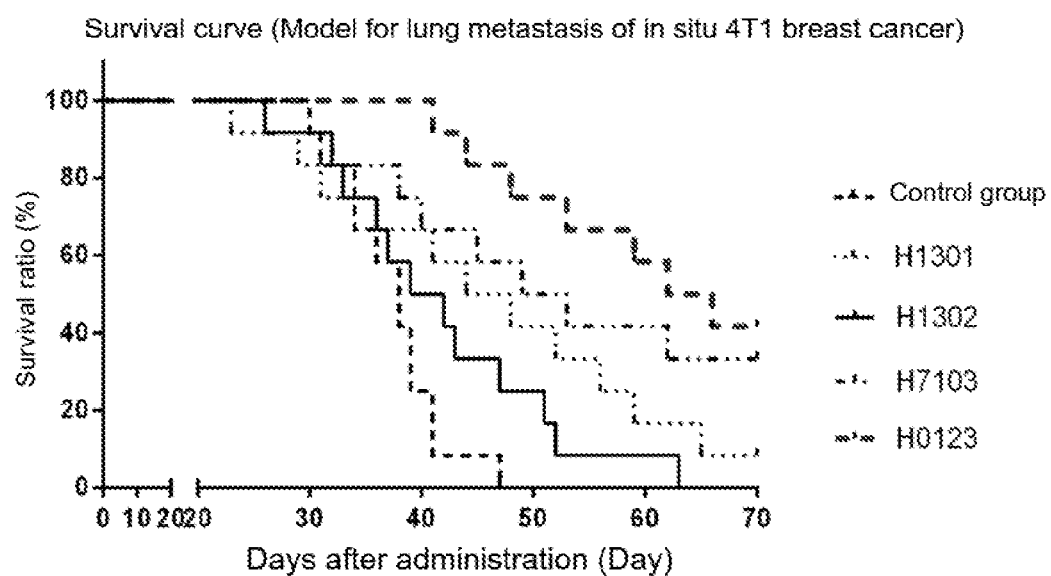

GLYCOSAMINOGLYCAN DERIVATIVE AND PREPARATION METHOD THEREFOR AND USE THEREOF

FIELD OF THE INVENTION

The present invention relates to a glycosaminoglycan derivative (particularly, a carboxylated glycosaminoglycan derivative), a preparation method therefor, and the use thereof for inhibiting tumor growth and/or metastasis.

BACKGROUND OF THE INVENTION

Heparanase, also known as heparitinase, is a β-endoglucuronidase that can cleave heparan sulfate (HS) in a heparan sulfate proteoglycan, such as syndecan-1, thereby releasing growth factors that bind to the heparan sulfate.

The heparanase is highly expressed in most human tumor cells, and significantly increases both angiogenesis and metastatic potential of tumor cells. Studies have confirmed that elevated heparanase level is correlated with advanced progression and metastasis of many tumor types. For example, a high level of heparanase is associated with a shorter post-operation survival time of patients. A direct role of heparanase in tumor metastasis has been demonstrated in Vlodaysky's and Sanderson's laboratory.

In addition to its enzymatic functions, that include release of HS-bound growth factors and degradation of the extracellular matrix (ECM), heparanase also has a non-enzymatic function that may impact tumor behavior and the microenvironment.

Heparin is a linear polydisperse sulfated polysaccharide of the glycosaminoglycan family, endowed with anticoagulant and antithrombotic activity. The saccharidic chains of heparin consist of alternating uronic acid and D-glucosamine, where the major repeating unit is 2-O-sulfated L-iduronic acid (IdoA2S)α(1→4) and N-, 6-O-disulfated D-glucosamine (GlcN6S); and the minor constituents are non-sulfated L-iduronic acid and D-glucuronic acid, along with N-acetyl D-glucosamine and N-, 3-O-, 6-O-trisulfated D-glucosamine (Casu B., 2005. "Structure and active domains of heparin." In: Chemistry and biology of heparin and heparan sulfate. Amsterdam: Elsevier. 1-28; Casu B. and Lindahl U., 2001, "Structure and biological interactions of heparin and heparan sulfate." Adv Carbohydr Chem Biochem, 57: 159-206). Heparin can effectively inhibit heparanase, but its use of heparin at high doses in a heparanase inhibition strategy is however impossible due to its anticoagulant activity.

Interestingly, low molecular weight heparins (LMWHs), which are more bioavailable and less anticoagulant than heparin, appear to prolong survival of patients with cancer, probably through a direct effect on tumor growth and metastasis. This may be due, at least in part, to inhibition of heparanase enzyme activity (Zacharski L. R., and Lee, A. Y. 2008. Heparin as an anticancer therapeutic. Expert Opin Investig Drugs 17:1029-1037).

The prior art has disclosed a class of non-anticoagulant heparins that can be used as heparanase inhibitors, most of which contain structurally modified non-sulfated uronic acid residues. Such structures may be obtained by opening of the glucosidic ring by cleavage of the linkage between carbons 2 and 3 of a glycosaminoglycan residue (glycol-splitting).

CN105744940A discloses carboxylated derivatives of glycosaminoglycans and anti-tumor use of the same.

SUMMARY OF THE INVENTION

The present invention provides a glycosaminoglycan derivative which has both anti-tumor growth and anti-tumor metastasis activity, especially good anti-tumor metastasis activity.

A first aspect of the present invention provides a glycosaminoglycan derivative comprising a structural unit of Formula (I), a structural unit of Formula (IV) and a structural unit of Formula (V):

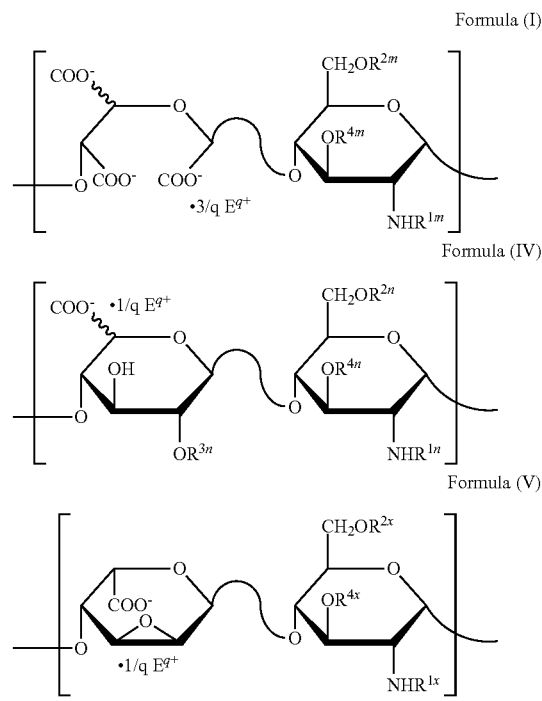

wherein:

$R^{1m}$, $R^{1n}$ and $R^{1x}$, at each occurrence, are each independently selected from the group consisting of H, $-SO_3^- \cdot (1/q\ E^{q+})$ and $-(C=O)CH_3$, and preferably, $R^{1m}$, $R^{1n}$ and $R^{1x}$, at each occurrence, are $SO_3^- \cdot (1/q\ E^{q+})$ or $-(C=O)CH_3$;

$R^{2m}$, $R^{2n}$ and $R^{2x}$, at each occurrence, are each independently selected from the group consisting of H and $-SO_3^- \cdot (1/q\ E^{q+})$;

$R^{3n}$, at each occurrence, is independently selected from the group consisting of H and $-SO_3^-\ (1/q\ E^{q+})$;

$R^{4m}$, $R^{4n}$ and $R^{4x}$, at each occurrence, are each independently selected from the group consisting of H and $-SO_3^- \cdot (1/q\ E^{q+})$;

E, at each occurrence, is independently selected from the group consisting of H, an alkali metal (preferably lithium, sodium, potassium, rubidium or cesium), an alkaline earth metal (preferably magnesium or calcium) and aluminum;

q, at each occurrence, is independently an integer of 1, 2, or 3;

the glycosaminoglycan derivative has a weight average molecular weight of 7000-14000 Da, preferably 8000-13500 Da, such as 8500-13000 Da, 8500-12500 Da or 9000-12500 Da; and the glycosaminoglycan derivative has a ring-opening degree of uronic acid of 25%-80%, preferably 25-60%.

A second aspect of the present invention provides a pharmaceutical composition comprising a prophylactically or therapeutically effective amount of the glycosaminoglycan derivative of the present invention and one or more pharmaceutically acceptable carriers, wherein the pharmaceutical composition is preferably in a form of a solid, semi-solid, liquid, or gas preparation.

A third aspect of the present invention provides use of the glycosaminoglycan derivative of the present invention or the pharmaceutical composition of the present invention in the manufacture of a medicament for inhibiting tumor growth and/or metastasis.

A fourth aspect of the present invention provides the glycosaminoglycan derivative of the present invention or the pharmaceutical composition of the present invention for use in inhibiting tumor growth and/or metastasis.

A fifth aspect of the present invention provides a method of inhibiting tumor growth and/or metastasis, comprising administering an effective amount of the glycosaminoglycan derivative of the present invention or the pharmaceutical composition of the present invention to a subject in need thereof.

A sixth aspect of the present invention provides a method for preparing the glycosaminoglycan derivative of the present invention.

BRIEF DESCRIPTION OF THE DRAWING

FIG. 1 shows the survival ratio of mice after administration of the test samples.

DETAILED DESCRIPTION OF THE INVENTION

As used herein, the term "sulfation degree" refers to the sulfo-carboxyl ratio ($SO_3^-/COO^-$ molar ratio) determined by conductimetric titration according to Casu B. and Gennaro U., 1975, Carbohydr Res 39, 168-176.

As used herein, the term "carboxyl increment" refers to the ratio of the sulfation degree of the starting material to the sulfation degree of the carboxylated derivative. More specifically, the sulfation degree of the starting material is the sulfation degree determined after reduction by $NaBH_4$ of the sample of the glycosaminoglycan intermediate obtained after the first oxidation step.

As used herein, the term "ring opening degree of uronic acid" refers to the number of the ring-opening uronic acid residues/the number of all uronic acid residues, and the term "epoxy degree of uronic acid" refers to the ratio of the uronic acid structural unit with an epoxy structure in Formula (V) to the total uronic acid residues. They are determined and calculated according to the nuclear magnetic method in Guerrini, M., Guglieri, S., Naggi, A., Sasisekharan, R., & Torri, G (2007). Low molecular weight heparins: Structural differentiation by bidimentional nuclear magnetic resonance spectroscopy. Seminars in Thrombosis and Hemostasis, 33, 478-487.

Glycosaminoglycan Derivative

In some embodiments, the present invention provides a glycosaminoglycan derivative comprising a structural unit of Formula (I), a structural unit of Formula (IV) and a structural unit of Formula (V):

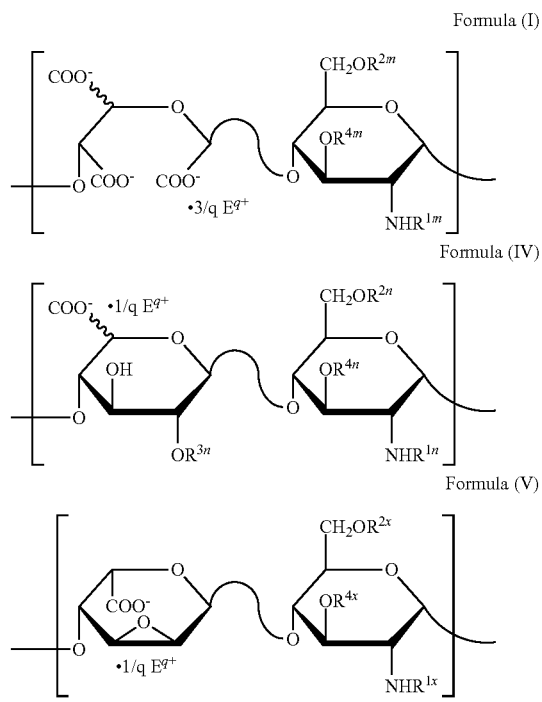

Formula (I)

Formula (IV)

Formula (V)

wherein:

$R^{1m}$, $R^{1n}$ and $R^{1x}$, at each occurrence, are each independently selected from the group consisting of H, —$SO_3^-$·(1/q $E^{q+}$) and —(C=O)$CH_3$, and preferably, $R^{1m}$, $R^{1n}$ and $R^{1x}$, at each occurrence, are $SO_3^-$·(1/q $E^{q+}$) or —(C=O)$CH_3$;

$R^{2m}$, $R^{2n}$ and $R^{2x}$, at each occurrence, are each independently selected from the group consisting of H and —$SO_3^-$·(1/q $E^{q+}$);

$R^{3n}$, at each occurrence, is independently selected from the group consisting of H and —$SO_3^-$·(1/q $E^{q+}$);

$R^{4m}$, $R^{4n}$ and $R^{4x}$, at each occurrence, are each independently selected from the group consisting of H and —$SO_3^-$·(1/q $E^{q+}$);

E, at each occurrence, is independently selected from the group consisting of H, an alkali metal (preferably lithium, sodium, potassium, rubidium or cesium), an alkaline earth metal (preferably magnesium or calcium) and aluminum;

q, at each occurrence, is independently an integer of 1, 2, or 3;

the glycosaminoglycan derivative has a weight average molecular weight of 7000-14000 Da, preferably 8000-13500 Da, such as 8500-13000 Da, 8500-12500 Da or 9000-12500 Da; and the glycosaminoglycan derivative has a ring-opening degree of uronic acid of 25%-80%, preferably 25%-60%.

In a preferred embodiment, the present invention provides a glycosaminoglycan derivative, further comprising a structural unit of Formula (II):

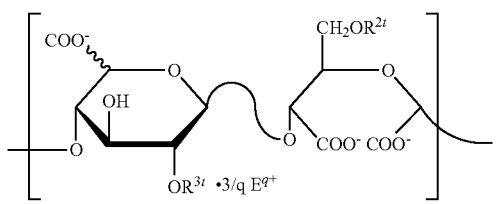

Formula (II)

wherein:

$R^{2t}$ and $R^{3t}$, at each occurrence, are each independently selected from the group consisting of H and $-SO_3^- \cdot (1/q\ E^{q+})$;

E, at each occurrence, is independently selected from the group consisting of H, an alkali metal (preferably lithium, sodium, potassium, rubidium or cesium), an alkaline earth metal (preferably magnesium or calcium) and aluminum; and q, at each occurrence, is independently an integer of 1, 2, or 3.

In a preferred embodiment, the present invention provides a glycosaminoglycan derivative, further comprising a structural unit of Formula (III):

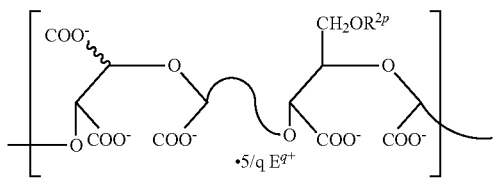

Formula (III)

wherein:

$R^{2p}$, at each occurrence, is independently selected from the group consisting of H and $-SO_3^- \cdot (1/q\ E^{q+})$;

E, at each occurrence, is independently selected from the group consisting of H, an alkali metal (preferably lithium, sodium, potassium, rubidium or cesium), an alkaline earth metal (preferably magnesium or calcium) and aluminum; and q, at each occurrence, is independently an integer of 1, 2, or 3.

In a preferred embodiment, the present invention provides a glycosaminoglycan derivative, further comprising a structural unit of Formula (VI):

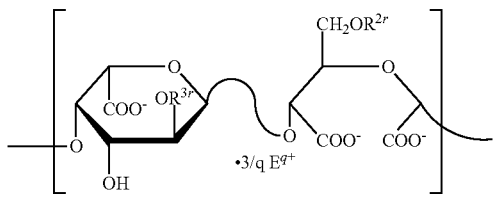

Formula (VI)

wherein:

$R^{2r}$ and $R^{3r}$, at each occurrence, are each independently selected from the group consisting of H and $-SO_3^- \cdot (1/q\ E^{q+})$;

E, at each occurrence, is independently selected from the group consisting of H, an alkali metal (preferably lithium, sodium, potassium, rubidium or cesium), an alkaline earth metal (preferably magnesium or calcium) and aluminum; and q, at each occurrence, is independently an integer of 1, 2, or 3.

In a preferred embodiment, the present invention provides a glycosaminoglycan derivative, further comprising a structural unit of Formula (VII):

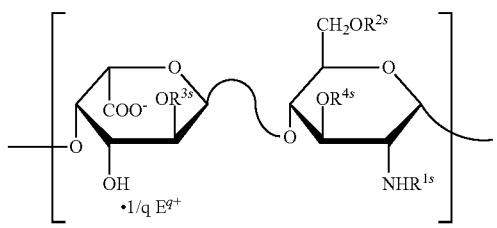

Formula (VII)

wherein:

$R^{1s}$, at each occurrence, is independently selected from the group consisting of H, $-SO_3^- \cdot (1/q\ E^{q+})$ and $-(C=O)CH_3$, and preferably $SO_3^- \cdot (1/q\ E^{q+})$ or $-(C=O)CH_3$;

$R^{2s}$, $R^{3s}$ and $R^{4s}$, at each occurrence, are each independently selected from the group consisting of H and $-SO_3^- \cdot (1/q\ E^{q+})$;

E, at each occurrence, is independently selected from the group consisting of H, an alkali metal (preferably lithium, sodium, potassium, rubidium or cesium), an alkaline earth metal (preferably magnesium or calcium) and aluminum; and q, at each occurrence, is independently an integer of 1, 2, or 3.

Optionally, one or more polysaccharide chains of the glycosaminoglycan derivative may each comprise m structural units of Formula (I), wherein m is selected from any integer of 1 to 30, inclusive; preferably selected from any integer of 1 to 20, inclusive.

Optionally, one or more polysaccharide chains of the glycosaminoglycan derivative may each comprise t structural units of Formula (II), wherein t is selected from any integer of 0 to 26, inclusive; preferably selected from any integer of 0 to 8, inclusive; more preferably selected from any integer of 1 to 8, inclusive.

Optionally, one or more polysaccharide chains of the glycosaminoglycan derivative may each comprise p structural units of Formula (III), wherein p is selected from any integer of 0 to 26, inclusive; preferably selected from any integer of 0 to 4, inclusive; more preferably selected from any integer of 1 to 4, inclusive.

Optionally, one or more polysaccharide chains of the glycosaminoglycan derivative may each comprise n structural units of Formula (IV), wherein n is selected from any integer of 1 to 24, inclusive; preferably selected from any integer of 1 to 18, inclusive.

Optionally, one or more polysaccharide chains of the glycosaminoglycan derivative may each comprise x structural units of Formula (V), wherein x is selected from any integer of 0 to 18, inclusive; preferably selected from any integer of 0 to 8, inclusive; more preferably selected from any integer of 1 to 8, inclusive.

Optionally, one or more polysaccharide chains of the glycosaminoglycan derivative may each comprise r structural units of Formula (VI), wherein r is selected from any integer of 0 to 26 (e.g., 1 to 26), inclusive; preferably selected from any integer of 0 to 4 (e.g., 1 to 4), inclusive.

Optionally, one or more polysaccharide chains of the glycosaminoglycan derivative may each comprise s structural units of Formula (VII), wherein s is selected from any integer of 1 to 26, inclusive; preferably selected from any integer of 1 to 8, inclusive.

In each polysaccharide chain of the glycosaminoglycan derivative of the present invention, the structural units are arranged in a random order.

In a preferred embodiment, $E^{q+}$ is $H^+$, $Li^+$, $Na^+$, $K^+$, $Mg^{2+}$, $Ca^{2+}$, or $Al^{3+}$.

In a preferred embodiment, the number of the structural unit of Formula (I) in the glycosaminoglycan derivative is greater than the sum of the numbers of the structural units of Formula (II) and Formula (III).

In a preferred embodiment, the ratio of the number of the structural unit of Formula (I) to the sum of the numbers of the structural units of Formula (I), Formula (II) and Formula (III) in the glycosaminoglycan derivative is greater than 0.9.

In a preferred embodiment, the ratio of the number of the structural unit of Formula (I) to the sum of the numbers of the structural units of Formula (I) and Formula (IV) in the glycosaminoglycan derivative is 0.3 to 0.7.

In a preferred embodiment, the ratio of the number of the structural unit of Formula (V) to the sum of the numbers of the structural units of Formula (I), Formula (IV) and Formula (V) in the glycosaminoglycan derivative is less than 0.1.

In a preferred embodiment, the epoxy degree of uronic acid is less than 25%.

In a preferred embodiment, the molecular weight distribution of the glycosaminoglycan derivative is as follows:

| Molecular weight range (Da) | Proportion (% by weight) |
| --- | --- |
| greater than 10000 | 15-80, preferably 25-80 |
| 6000-10000 | 15-50 |
| less than 6000 | 5-50 |

In a preferred embodiment, the molecular weight distribution of the glycosaminoglycan derivative is as follows:

| Molecular weight range (Da) | Proportion (% by weight) |
| --- | --- |
| greater than 10000 | 30-75 |
| 6000-10000 | 20-40 |
| less than 6000 | 5-30 | or

| Molecular weight range (Da) | Proportion (% by weight) |
| --- | --- |
| greater than 10000 | 30-75 |
| 6000-10000 | 20-40 |
| less than 6000 | 0-30 |

In a preferred embodiment, the glycosaminoglycan derivative has a sulfo-carboxyl ratio of 0.80-1.65. Preferably, the glycosaminoglycan derivative has a sulfo-carboxyl ratio of 1.0-1.4.

The invention encompasses any combination of various embodiments.

In some embodiments, the present invention provides a method for preparing the glycosaminoglycan derivative, comprising the following steps:

a) optionally, performing C2, C3 epoxidation of the uronic acid residues in the glycosaminoglycan, preferably in an alkaline aqueous solution (preferably an aqueous solution of sodium hydroxide);

b) optionally, hydrolyzing the epoxidation product obtained in step a) with ring opening, preferably under a neutral condition;

c) under a condition effective to convert adjacent diols and optionally adjacent $OH/NH_2$ to dialdehydes, oxidizing 10%-100% (preferably 25%-100%) of 2-O—, and optionally 2N-, 3-O-, non-sulfated residues of the glycosaminoglycan, wherein the oxidation is preferably performed by periodate (preferably sodium periodate); and d) under a condition effective to convert the dialdehydes to carboxyl groups and without nitrogen protection, further oxidizing the product obtained in step c), wherein the further oxidation is preferably performed by chlorite (preferably sodium chlorite).

In a preferred embodiment, the method further comprises a step of 2N-desulfation of the glucosamine residues before step a), after step a), or after step b), wherein the desulfation step comprises salt formation with pyridine, followed by stirring in a mixed solvent of DMSO and water or methanol.

In a preferred embodiment, the glycosaminoglycan is natural or synthetic heparin (optionally chemically or enzymatically modified) from any animal and organ sources, preferably selected from the group consisting of optionally 2-O- and/or 2-N-desulfated heparin, unfractionated heparin, low molecular weight heparin (LMWH, with a molecular weight of 3,500-8,000 Da) and heparan sulfate (HS), with a sulfo-carboxyl ratio of 0.8-2.8, preferably 0.9-2.5; more preferably, selected from the group consisting of optionally 2-O- and/or 2-N-desulfated unfractionated heparin and LMWH.

In a preferred embodiment, the glycosaminoglycan has a weight average molecular weight of 10000 Da to 30000 Da, preferably 15000 Da to 25000 Da, such as 15000 Da to 20000 Da, 15000 Da to 19000 Da, or 17000 Da to 19000 Da.

As an example, heparin chains can naturally comprise from about 5% to 35% of 2-O-non-sulfated uronic acid residues, from 0% to 50% of N-acetylated glucosamine residues, and from about 0%-6% of N-unsubstituted (neither N-sulfated nor N-acetylated) glucosamine residues. Different sulfation degree depends on the heparin source (animal species, organ sources) and on the extraction procedures.

Every 2-O- or 2N-non-sulfated residue of glycosaminoglycans, not bearing 3-O-sulfate substituents, is susceptible of oxidation with ring opening (split) and conversion of vicinal diols and $OH/NH_2$ to aldehydes. Optionally, graded 2-O-desulfation of the starting glycosaminoglycans allows to modulate the ratio of glucosamine/uronic acid split residues.

In a preferred embodiment, the glycosaminoglycan derivative exhibits a carboxyl increment of 1.3-2.0, wherein said carboxyl increment is calculated as the ratio of the sulfation degree of the starting material to the sulfation degree of the glycosaminoglycan derivative. More specifically, the sulfation degree of the starting material is the sulfation degree determined after reduction by $NaBH_4$ of the sample of the glycosaminoglycan intermediate obtained after the first oxidation step (step c). The specific procedures for calculating the carboxyl increment may be found in CN105744940A.

Pharmaceutical Composition and Therapeutic Method

In some embodiments, the present invention provides a pharmaceutical composition comprising a prophylactically or therapeutically effective amount of the glycosaminoglycan derivative of the present invention and one or more pharmaceutically acceptable carriers, wherein the pharmaceutical composition is preferably in a form of a solid, semi-solid, liquid, or gas preparation. In some embodiments, the pharmaceutical composition may further comprise one or more additional therapeutic agents.

In some embodiments, the present invention provides use of the glycosaminoglycan derivative of the present invention or the pharmaceutical composition of the present invention in the manufacture of a medicament for inhibiting tumor growth and/or metastasis.

In some embodiments, the present invention provides the glycosaminoglycan derivative of the present invention or the pharmaceutical composition of the present invention for use in inhibiting tumor growth and/or metastasis.

In some embodiments, the present invention provides a method of inhibiting tumor growth and/or metastasis, comprising administering an effective amount of the glycosaminoglycan derivative of the present invention or the pharmaceutical composition of the present invention to a subject in need thereof.

In some embodiments, the tumor is a solid tumor, a hematological tumor, or a soft tissue tumor; preferably a solid tumor, e.g., breast cancer, pancreatic cancer, bladder cancer, prostate cancer, colon cancer, gastric cancer or lung cancer.

The term "pharmaceutically acceptable carrier" in the present invention refers to a diluent, auxiliary material, excipient, or vehicle with which a therapeutic is administered, and it is, within the scope of sound medical judgment, suitable for contact with the tissues of human beings and animals without excessive toxicity, irritation, allergic response, or other problem or complication, commensurate with a reasonable benefit/risk ratio.

The pharmaceutically acceptable carrier which can be employed in the pharmaceutical composition of the present invention includes, but is not limited to sterile liquids, such as water and oils, including those of petroleum, animal, vegetable or synthetic origin, such as peanut oil, soybean oil, mineral oil, sesame oil and the like. Water is an exemplary carrier when the pharmaceutical composition is administered intravenously. Physiological salines as well as aqueous dextrose and glycerol solutions can also be employed as liquid carriers, particularly for injectable solutions. Suitable pharmaceutical excipients include starch, glucose, lactose, sucrose, gelatin, maltose, chalk, silica gel, sodium stearate, glycerol monostearate, talc, sodium chloride, dried skim milk, glycerol, propylene glycol, water, ethanol and the like. The pharmaceutical composition, if desired, can also contain minor amounts of wetting or emulsifying agents, or pH buffering agents. Oral formulations can include standard carriers such as pharmaceutical grades of mannitol, lactose, starch, magnesium stearate, sodium saccharine, cellulose, magnesium carbonate, etc. Examples of suitable pharmaceutical carriers are described in e.g. Remington's Pharmaceutical Sciences (1990).

The pharmaceutical composition of the present invention can act systemically and/or topically. To this end, it can be administered through a suitable route, such as through injection, (intravenous, intraarterial, subcutaneous, intraperitoneal, intramuscular injection, including dripping), or transdermal administration, or administered via oral, buccal, nasal, transmucosal, topical, as an ophthalmic formulation, or via inhalation.

For these routes of administration, the pharmaceutical composition of the present invention can be administered in a suitable dosage form.

Such dosage forms include, but are not limited to tablets, capsules, lozenges, hard candies, powders, sprays, creams, salves, suppositories, gels, pastes, lotions, ointments, aqueous suspensions, injectable solutions, elixirs, and syrups.

As used herein, the term "effective amount" refers to the amount of a derivative being administered which will relieve to some extent one or more of the symptoms of the disorder being treated.

Dosage regimens may be adjusted to provide the optimum desired response. For example, a single bolus may be administered, several divided doses may be administered over time, or the dose may be proportionally reduced or increased as indicated by the exigencies of the therapeutic situation. It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the composition.

The amount of the glycosaminoglycan derivative of the present invention administered will be dependent on the subject being treated, the severity of the disorder or condition, the rate of administration, the disposition of the glycosaminoglycan derivative and the discretion of the prescribing physician. Generally, an effective dosage is in the range of about 0.0001 mg to about 50 mg per kg body weight per day, for example about 0.01 mg/kg/day to about 10 mg/kg/day, in single or divided doses. For a 70 kg human, this would amount to about 0.007 mg to about 3500 mg/day, for example about 0.7 mg to about 700 mg/day. In some instances, dosage levels below the lower limit of the aforesaid range may be more than adequate, while in other cases, still larger doses may be employed without causing any harmful side effect, provided that such larger doses are first divided into several small doses for administration throughout the day.

The content or dosage of the glycosaminoglycan derivative of the present invention in the pharmaceutical composition is about 0.01 mg to about 1000 mg, suitably 0.1-500 mg, preferably 0.5-300 mg, more preferably 1-150 mg, particularly preferably 1-50 mg, e.g., 1.5 mg, 2 mg, 4 mg, 10 mg, 25 mg, etc.

Unless otherwise indicated, the term "treating" or "treatment", as used herein, means reversing, alleviating, inhibiting the progress of, or preventing the disorder or condition to which such term applies, or one or more symptoms of such disorder or condition.

As used herein, the term "subject" includes a human or non-human animal. An exemplary human subject includes a human subject having a disease (such as one described herein) (referred to as a patient), or a normal subject. The term "non-human animal" as used herein includes all vertebrates, such as non-mammals (e.g. birds, amphibians, reptiles) and mammals, such as non-human primates, livestock and/or domesticated animals (such as sheep, dog, cat, cow, pig and the like).

In some embodiments, the pharmaceutical composition of the present invention can further comprise one or more additional therapeutic agents or prophylactic agents.

EXAMPLES

Examples and experimental examples are given below to further illustrate the present invention in detail, but do not limit the scope of the present invention. Also, modification can be made without departing from the scope of the present invention.

Example 1

1) C2 and C3 epoxidation: 5 g unfractionated heparin (Mw=18306 Da) was weighed and dissolved in 62.5 g of a 1 mol/L NaOH solution. The reaction solution was heated to 60° C. and reacted for 30 min After the reaction was complete, it was cooled at room temperature and neutralized with a 1:1 HCl solution (prepared by mixing a commercially available 36%-38% concentrated hydrochloric acid with purified water at a volume ratio of 1:1).

2) Hydrolysis with ring opening: the solution in step 1) was heated to 70° C., and hydrolyzed under a neutral condition for 36 hours. After the reaction was complete, the reaction solution was cooled to room temperature.

3) Oxidation by sodium periodate: the reaction solution in step 2) was added with 100 g of a 0.2 mol/L $NaIO_4$ solution under a low temperature condition, and stirred for 16 h while being protected from light with the temperature maintained at 4° C. After the reaction was complete, it was quenched by adding 10.0 mL ethylene glycol and stirring for another 1 h. The reaction solution was dialyzed (desalting) for 24 h to obtain dialysate.

4) Oxidation by sodium chlorite: 100 g of a 6.03% (m/v) $NaClO_2$ solution was added to the reaction solution obtained in step 3) under a low temperature condition. The reaction was adjusted to pH of about 4.0 with glacial acetic acid, and stirred at room temperature for 24 h. The reaction was neutralized with a 30% (m/v) NaOH solution. The reaction solution was dialyzed for 24 hours. The dialysate was concentrated by rotary evaporation and lyophilized to obtain sample H0242. Yield: 88.45%, Mw=7001 Da, $SO_3^-/COO^-$=0.85. The carboxyl increment was 1.88, and the ring opening degree of uronic acid was 73.1%.

Example 2

1) Oxidation by sodium periodate: 5 g of unfractionated heparin (Mw=17000 Da) was weighed, placed in 250 g water, and stirred to dissolve. 100 g of a 0.2 mol/L $NaIO_4$ solution was added under a low temperature condition, and stirred for 16 h while being protected from light with the temperature maintained at 4° C. After the reaction was complete, it was quenched by adding 10.0 mL ethylene glycol and stirring for another 1 h. The reaction solution was then dialyzed for 24 h to obtain dialysate.

2) Oxidation by sodium chlorite: the dialysate obtained in step 1) was taken and added under a low temperature condition to 100 g of a 6.03% (m/v) $NaClO_2$ solution. The reaction was adjusted to pH of about 4.0 with glacial acetic acid, and stirred at room temperature for 24 h. The reaction was neutralized with a 30% (m/v) NaOH solution. The reaction solution was dialyzed for 24 h. The dialysate was concentrated by rotary evaporation and lyophilized to obtain sample H0232. Yield: 79.23%, Mw=12810 Da, $SO_3^-/COO^-$=1.55. The carboxyl increment was 1.22, and the ring opening degree of uronic acid was 26.3%.

Example 3

1) C2 and C3 epoxidation: 50 g unfractionated heparin (Mw=17000 Da) was weighed and added to 625.0 g of a 1 mol/L NaOH solution. The reaction solution was heated to about 60° C. and reacted for 30 min After the reaction was complete, it was cooled at room temperature and neutralized with a 1:1 HCl solution (prepared by mixing a commercially available 36%-38% concentrated hydrochloric acid with purified water at a volume ratio of 1:1).

2) Hydrolysis with ring opening: the solution in step 1) was heated to 70° C., and hydrolyzed under a neutral condition for 24 hours. After the reaction was complete, the reaction solution was cooled to room temperature. A sample of the solution was taken to determine the molecular weight. The mixture was desalted by dialysis, rotary evaporated and lyophilized to obtain an intermediate product. The dry product weighed 50 g, the yield was 100%, and Mw=16034 Da.

3) Oxidation by sodium periodate: 5 g of the intermediate product obtained in step 2) was taken and dissolved in 100 g of water. Under a low temperature condition, 233 g of a 0.2 mol/L $NaIO_4$ solution was added and stirred for 8 h, while the reaction was protected from light with the temperature maintained at 4° C. After the reaction was complete, it was quenched by adding 20.0 mL ethylene glycol and stirring for another 1 h. The reaction solution was dialyzed (desalting) for 24 h to obtain dialysate.

4) Oxidation by sodium chlorite: 100 g of a 6.03% (m/v) $NaClO_2$ solution was added to the reaction solution obtained in step 3) under a low temperature condition. The reaction was adjusted to pH of about 4.0 with glacial acetic acid, and stirred at room temperature for 24 h. The reaction was neutralized with a 30% (m/v) NaOH solution. The reaction solution was dialyzed for 24 hours. The dialysate was concentrated by rotary evaporation and lyophilized to obtain sample H1011. Yield: 89.90%, Mw=9161 Da, $SO_3^-/COO^-$=1.17. The carboxyl increment was 1.68, and the ring opening degree of uronic acid was 43.1%.

Example 4

1) Same as step 1) of Example 3.
2) Same as step 2) of Example 3.
3) Oxidation by sodium periodate: 5 g of the intermediate product obtained in step 2) was taken and dissolved in 100 g of water. Under a low temperature condition, 116 g of a 0.2 mol/L $NaIO_4$ solution was added, and stirred for 16 h, while the reaction was protected from light with the temperature maintained at 4° C. After the reaction was complete, it was quenched by adding 20.0 mL ethylene glycol and stirring for another 1 h. The reaction solution was dialyzed (desalting) for 24 h to obtain dialysate.
4) Same as step 4) of Example 3. The obtained sample H1015 has a yield of 89.69%, Mw=8717 Da, $SO_3^-/COO^-$=1.08, a carboxyl increment of 1.81, and a ring opening degree of uronic acid of 45.5%.

Example 5

1) C2 and C3 epoxidation: 8 g unfractionated heparin (Mw=18150 Da) was weighed and added to a 1 mol/L NaOH solution (about 102.4 mL). The reaction solution was heated to about 60° C. and reacted for 30 min. After the reaction was complete, it was cooled at room temperature and neutralized with a 1:1 HCl solution (prepared by mixing a commercially available 36%-38% concentrated hydrochloric acid with purified water at a volume ratio of 1:1). Ethyl alcohol was added to the reaction solution for alcohol precipitation, and the precipitate was dissolved and lyophilized.

2) Hydrolysis with ring opening: 6.4 g of the lyophilized product in step 1) was weighed, and 96 mL of purified water was added. The solution was heated to 70° C., and hydrolyzed under a neutral condition for 24 h. After the reaction was complete, it was cooled at room temperature, concentrated and lyophilized to obtain a product with a ring-opened epoxy structure.

3) Oxidation by sodium periodate: 177 mL of purified water was added to dissolve 6.14 g of the product with a ring-opened epoxy structure in step 2), and an equal volume of a 0.2 mol/L $NaIO_4$ solution was added at a low temperature condition. It was stirred for 16 h while being protected from light with the temperature maintained at 4° C. After the reaction was complete, it was quenched by adding 17.7 mL ethylene glycol and stirring for another 1 h. Ethyl alcohol was added to the reaction solution for alcohol precipitation (desalting). The supernatant obtained from the alcohol precipitation was centrifuged. The precipitates were combined, dissolved with a small amount of water, and lyophilized to obtain a vicinal dialdehyde intermediate.

4) Oxidation by sodium chlorite: 579 mL of purified water was added to the vicinal dialdehyde intermediate (6 g). The reaction solution was cooled, added with 120 mL of a 6.03% (m/v) $NaClO_2$ solution, and adjusted to pH of about 4.0 with glacial acetic acid. The reaction was stirred at room temperature and reacted for 24 hours, and then neutralized with a 1 mol/L NaOH solution. Sodium bisulfite solid was added in portions to neutralize sodium chlorite. Ethyl alcohol was added to the reaction solution for alcohol precipitation. After the precipitate was dissolved, it was dialyzed with a regenerated cellulose dialysis bag having a molecular weight cutoff of 3500 Da. The dialysate was concentrated by rotary evaporation and lyophilized to obtain sample H7103. Mw=11790 Da, $SO_3^-/COO^-$=1.26. The carboxyl increment was 1.75, and the ring opening degree of uronic acid was 41.2%.

Example 6

1) C2 and C3 epoxidation: 10 g unfractionated heparin (Mw=17675 Da) was weighed and dissolved in 125 g of a 1 mol/L NaOH solution. The reaction solution was heated to about 60° C. and reacted for 30 min After the reaction was complete, it was cooled at room temperature, and then neutralized with a 1:1 HCl solution (prepared by mixing a commercially available 36%-38% concentrated hydrochloric acid with purified water at a volume ratio of 1:1).

2) Hydrolysis with ring opening: the solution in step 1) was heated to 70° C., and hydrolyzed under a neutral condition for 24 hours. After the reaction was complete, the reaction solution was cooled to room temperature.

3) Oxidation by sodium periodate: 200 g of a 0.2 mol/L $NaIO_4$ solution was added under a low temperature condition to the reaction solution in step 2), and the solution was stirred for 16 h while being protected from light with the temperature maintained at 4° C. After the reaction was complete, it was quenched by adding 20.0 mL ethylene glycol and stirring for another 1 h. The solution was dialyzed for 24 h (desalting) to obtain dialysate.

4) Oxidation by sodium chlorite: 200 g of a 6.03% (m/v) $NaClO_2$ solution was added to the reaction solution obtained in step 3) under a low temperature condition, and the mixture was adjusted to pH of about 4.0 with glacial acetic acid. The reaction was stirred at room temperature and reacted for 24 h, and then neutralized with a 30% (m/v) NaOH solution. The reaction solution was dialyzed for 24 h. The dialysate was concentrated by rotary evaporation and lyophilized to obtain sample H8261. Mw=10222 Da, $SO_3^-/COO^-$=1.05. The ring opening degree of uronic acid was 57.6%.

Example 7

1) C2 and C3 epoxidation: 10 g unfractionated heparin (Mw=17806 Da) was weighed and dissolved in 125 g of a 1 mol/L NaOH solution. The reaction solution was heated to about 60° C. and reacted for 60 min After the reaction was complete, it was cooled at room temperature and neutralized with a 1:1 HCl solution (prepared by mixing a commercially available 36%-38% concentrated hydrochloric acid with purified water at a volume ratio of 1:1).

2) Hydrolysis with ring opening: the solution in step 1) was heated to 70° C., and hydrolyzed under a neutral condition for 24 hours. After the reaction was complete, the reaction solution was cooled to room temperature.

3) Oxidation by sodium periodate: 200 g of a 0.2 mol/L $NaIO_4$ solution was added under a low temperature condition to the reaction solution in step 2), and the solution was stirred for 16 h while being protected from light with the temperature maintained at 4° C. After the reaction was complete, it was quenched by adding 20.0 mL ethylene glycol and stirring for another 1 h. The reaction solution was then dialyzed for 24 h.

4) Oxidation by sodium chlorite: 200 g of a 6.03% (m/v) $NaClO_2$ solution was added to the reaction solution obtained in step 3) under a low temperature condition, and the mixture was adjusted to pH of about 4.0 with glacial acetic acid. It was stirred at room temperature and reacted for 24 h, and then neutralized with a 30% (m/v) NaOH solution. The reaction solution was dialyzed for 24 h. The dialysate was concentrated by rotary evaporation and lyophilized to obtain sample H9053. Mw=7112 Da, $SO_3^-/COO^-$=1.13. The ring opening degree of uronic acid was 46.1%.

Example 8

1) C2 and C3 epoxidation: 10 g unfractionated heparin (Mw=18306 Da) was weighed and dissolved in 125 g of a 1 mol/L NaOH solution. The reaction solution was heated to about 60° C. and reacted for 30 min After the reaction was complete, it was cooled at room temperature and neutralized with a 1:1 HCl solution (prepared by mixing a commercially available 36%-38% concentrated hydrochloric acid with purified water at a volume ratio of 1:1). The solution was dialyzed for 16 h.

2) Hydrolysis with ring opening: the solution in step 1) was heated to 70° C., and hydrolyzed under a neutral condition for 4 hours. After the reaction was complete, the reaction solution was cooled to room temperature.

3) Oxidation by sodium periodate: 200 g of a 0.2 mol/L $NaIO_4$ solution was added under a low temperature condition to the reaction solution in step 2), and the solution was stirred for 16 h while being protected from light with the temperature maintained at 4° C. After the reaction was complete, it was quenched by adding 20.0 mL ethylene glycol and stirring for another 1 h. Ethyl alcohol was added to the reaction solution for alcohol precipitation (desalting). The supernatant obtained after alcohol precipitation was centrifuged, and the precipitates were combined and dissolved with a small amount of water.

4) Oxidation by sodium chlorite: 200 g of a 6.03% (m/v) $NaClO_2$ solution was added to the reaction solution obtained in step 3) under a low temperature condition, and the mixture was adjusted to pH of about 4.0 with glacial acetic acid. The reaction was stirred at room temperature and reacted for 24 h, and then neutralized with a 30% (m/v) NaOH solution. The reaction solution was dialyzed for 24 h. The dialysate was concentrated by rotary evaporation and lyophilized to obtain sample H8073. Mw=11781 Da, $SO_3^-/COO^-$=1.38. The carboxyl increment was 1.41, and the ring opening degree of uronic acid was 28.5%.

Example 9

1) C2 and C3 epoxidation: 5 g unfractionated heparin (Mw=17000 Da) was weighed and dissolved in 62.5 g of a 1 mol/L NaOH solution. The reaction solution was heated to 60° C. and reacted for 30 min After the reaction was complete, it was cooled at room temperature and neutralized with a 1:1 HCl solution (prepared by mixing a commercially available 36%-38% concentrated hydrochloric acid with purified water at a volume ratio of 1:1).

2) Hydrolysis with ring opening: the solution in step 1) was heated to 70° C., and hydrolyzed under a neutral condition for 24 hours. After the reaction was complete, the reaction solution was cooled to room temperature.

3) Oxidation by sodium periodate: 100 g of a 0.2 mol/L $NaIO_4$ solution was added under a low temperature condition to the reaction solution in step 2), and the solution was stirred for 16 h while being protected from light with the temperature maintained at 4° C. After the reaction was complete, it was quenched by adding 10.0 mL ethylene glycol and stirring for another 1 h. The reaction solution was then dialyzed.

4) Oxidation by sodium chlorite: 100 g of a 6.03% (m/v) $NaClO_2$ solution was added to the reaction solution obtained in step 3) under a low temperature condition, and the mixture was adjusted to pH of about 4.0 with glacial acetic acid. It was stirred at room temperature and reacted for 24 h, and then neutralized with a 30% (m/v) NaOH solution. The reaction solution was dialyzed for 24 h. The dialysate was concentrated by rotary evaporation and lyophilized to obtain sample H9252. Mw=8587 Da, $SO_3^-/COO^-$=1.10. The carboxyl increment was 1.76, and the ring opening degree of uronic acid was 46.6%.

Example 10

1) C2 and C3 epoxidation: 5 g unfractionated heparin (Mw=18306 Da) was weighed and dissolved in 62.5 g of a 1 mol/L NaOH solution. The reaction solution was heated to 60° C. and reacted for 30 min After the reaction was complete, it was cooled at room temperature and neutralized with a 1:1 HCl solution (prepared by mixing a commercially available 36%-38% concentrated hydrochloric acid with purified water at a volume ratio of 1:1).

2) Hydrolysis with ring opening: the solution in step 1) was heated to 70° C., and hydrolyzed under a neutral condition for 24 hours. After the reaction was complete, the reaction solution was cooled to room temperature.

3) Oxidation by sodium periodate: 100 g of a 0.2 mol/L $NaIO_4$ solution was added under a low temperature condition to the reaction solution in step 2), and the solution was stirred for 16 h while being protected from light with the temperature maintained at 4° C. After the reaction was complete, it was quenched by adding 10.0 mL ethylene glycol and stirring for another 1 h. The reaction solution was then dialyzed.

4) Oxidation by sodium chlorite: 100 g of a 6.03% (m/v) $NaClO_2$ solution was added to the reaction solution obtained in step 3) under a low temperature condition, and the mixture was adjusted to pH of about 4.0 with glacial acetic acid. It was stirred at room temperature and reacted for 24 h, and then neutralized with a 30% (m/v) NaOH solution. The reaction solution was dialyzed for 24 h. The dialysate was concentrated by rotary evaporation and lyophilized to obtain sample H0123. Mw=11445 Da, $SO_3^-/COO^-$=1.21. The carboxyl increment was 1.64, and the ring opening degree of uronic acid was 33.2%.

Example 11

1) C2 and C3 epoxidation: 4 g unfractionated heparin (Mw=18839 Da) was weighed and added with a 1 mol/L NaOH solution (about 51.2 mL). The reaction solution was heated to 60° C. and reacted for 30 min. After the reaction was complete, it was cooled at room temperature and neutralized with a 1:1 HCl solution (prepared by mixing a commercially available 36%-38% concentrated hydrochloric acid with purified water at a volume ratio of 1:1). The reaction solution was dialyzed for 72 h, concentrated and lyophilized.

2) Hydrolysis with ring opening: 3 g of the lyophilized product in step 1) was weighed, and 45 mL of purified water was added. The solution was heated to 70° C., and hydrolyzed under a neutral condition for 48 h. After the reaction was complete, the reaction was cooled to room temperature, concentrated and lyophilized to obtain a product with a ring-opened epoxy structure.

3) Oxidation by sodium periodate: the product with a ring-opened epoxy structure (2 g) in step 2) was dissolved by adding 57.7 mL of purified water, and an equal volume of a 0.2 mol/L $NaIO_4$ solution was added at a low temperature condition. It was further stirred for 16 h while being protected from light with the temperature maintained at 4° C. After the reaction was complete, it was quenched by adding 5.77 mL ethylene glycol and stirring for another 1 h. The reaction solution was dialyzed at 4° C. for 16 h, concentrated, and lyophilized to obtain a vicinal dialdehyde intermediate.

4) Oxidation by sodium chlorite: 100 mL of purified water was added to the vicinal dialdehyde intermediate (1 g). The reaction solution was cooled to 0° C., added with 20.6 mL of a 6.03% (m/v) $NaClO_2$ solution, and adjusted to pH of 4.0 with glacial acetic acid. It was stirred at room temperature and reacted for 24 hours, and then neutralized with 0.5 mol/L NaOH solution. The reaction solution was dialyzed for 16 h with a regenerated cellulose dialysis bag having a molecular weight cutoff of 3500 Da. The dialysate was concentrated by rotary evaporation and lyophilized to obtain sample H1301. Mw=7064 Da, $SO_3^-/COO^-$=1.06. The carboxyl increment was 1.75 and the ring opening degree of uronic acid was 28.9%.

Comparative Example (Since the Weight Average Molecular Weight of the Starting Material is not Specified in CN105744940A, a Person Skilled in the Art Cannot Obtain its Product for Comparison. This Comparative Example is the Product Obtained by Repeating the Procedures in Example 1, Example 4, and Example 8 in CN105744940A, and its Characterization Parameters were Slightly Different from Those of Example 8 in CN105744940A.)

1) C2 and C3 epoxidation: 4 g unfractionated heparin (Mw=18839 Da) was weighed and added with a 1 mol/L NaOH solution (about 51.2 mL). The reaction solution was heated to 60° C. and reacted for 30 min. After the reaction was complete, it was cooled at room temperature and neutralized with a 1:1 HCl solution (prepared by mixing a commercially available 36%-38% concentrated hydrochloric acid with purified water at a volume ratio of 1:1). The reaction solution was dialyzed for 72 h, concentrated and lyophilized.

2) Hydrolysis with ring opening: 3.0 g of the lyophilized product in step 1) was weighed, and 45 mL of purified water was added. The solution was heated to 70° C., and hydrolyzed under a neutral condition for 48 h. After the reaction was complete, the reaction solution was cooled to room temperature, concentrated and lyophilized to obtain a product with a ring-opened epoxy structure.

3) Oxidation by sodium periodate: the product with a ring-opened epoxy structure (2 g) in step 2) was dissolved by adding 57.7 mL of purified water, and an equal volume of a 0.2 mol/L $NaIO_4$ solution was added at low temperature. It was further stirred for 16 h while being protected from light with the temperature maintained at 4° C. After the reaction was complete, it was quenched by adding 5.77 mL ethylene glycol and stirring for another 1 h. The reaction solution was dialyzed at 4° C. for 16 h, concentrated, and lyophilized to obtain a vicinal dialdehyde intermediate.

4) Oxidation by sodium chlorite: 100 mL of purified water was added to the vicinal dialdehyde intermediate (1 g). The reaction solution was cooled to 0° C., and 20.6 mL of a 6.03% (m/v) $NaClO_2$ solution was added under stirring in a $N_2$ atmosphere. The pH was adjusted to 4.0 with glacial acetic acid. The reaction was stirred at room temperature and reacted for 24 h. After further 3 hours under stirring at room temperature, by fluxing Na, the reaction mixture was neutralized with a 0.5 mol/L NaOH solution. The reaction solution was dialyzed for 16 h with a regenerated cellulose dialysis bag having a molecular weight cutoff of 3500 Da. The dialysate was concentrated by rotary evaporation and lyophilized to obtain sample H1302. Mw=6499 Da, $SO_3^-$/$COO^-$=1.24. The carboxyl increment was 1.34 and the ring opening degree of uronic acid was 22.6%.

The physical and chemical property data of the products obtained in the above examples and comparative example are summarized in Table 1.

TABLE 1

| Sample No. | Weight average molecular weight (Da) | Ring opening degree of uronic acid | Epoxy degree of uronic acid | Sulfo-carboxyl ratio | Carboxyl increment |
|---|---|---|---|---|---|
| H0242 | 7001 | 73.1% | 3.1% | 0.85 | 1.88 |
| H0232 | 12810 | 26.3% | 0.3% | 1.55 | 1.22 |
| H1011 | 9161 | 43.1% | 4.8% | 1.17 | 1.68 |
| H1015 | 8717 | 45.5% | 4.8% | 1.08 | 1.81 |

TABLE 1-continued

| Sample No. | Weight average molecular weight (Da) | Ring opening degree of uronic acid | Epoxy degree of uronic acid | Sulfo-carboxyl ratio | Carboxyl increment |
|---|---|---|---|---|---|
| H7103 | 11790 | 41.2% | 19.8% | 1.26 | 1.75 |
| H8261 | 10222 | 57.6% | 3.3% | 1.05 | N/A |
| H9053 | 7112 | 46.1% | 5.1% | 1.13 | N/A |
| H8073 | 11781 | 28.5% | 21.3% | 1.38 | 1.41 |
| H9252 | 8587 | 46.6% | 4.6% | 1.10 | 1.76 |
| H0123 | 11445 | 33.2% | 17.6% | 1.21 | 1.64 |
| H1301 | 7064 | 28.9% | 3.9% | 1.06 | 1.75 |
| H1302 | 6499 | 22.6% | 4.7% | 1.24 | 1.34 |

N/A means not detected.

The molecular weight distribution data of the prepared products are shown in Table 2.

TABLE 2

| Sample No. | Weight average molecular weigh | >10000 | 8000-10000 | 6000-8000 | <6000 |
|---|---|---|---|---|---|
| H0242 | 7001 | 17.6 | 13.9 | 20.3 | 48.2 |
| H0232 | 12810 | 59.5 | 14.0 | 12.7 | 13.8 |
| H1011 | 9161 | 36.2 | 17.9 | 19.6 | 26.3 |
| H1015 | 8717 | 32.2 | 17.9 | 20.6 | 29.3 |
| H7103 | 11790 | 56.0 | 17.0 | 14.2 | 12.8 |
| H8261 | 10222 | 44.9 | 17.8 | 17.6 | 19.7 |
| H9053 | 7112 | 18.3 | 15.5 | 22.0 | 44.2 |
| H8073 | 11781 | 58.8 | 15.8 | 12.5 | 12.9 |
| H9252 | 8587 | 31.4 | 17.7 | 20.8 | 30.1 |
| H0123 | 11445 | 55.4 | 16.6 | 14.1 | 13.8 |
| H1301 | 7064 | 18.0 | 14.6 | 21.1 | 46.3 |
| H1302 | 6499 | 14.1 | 12.5 | 18.6 | 54.8 |

By comparing products H1301 and H1302, it can be seen that the product of the present application is significantly different from the product obtained by the process in CN105744940A (especially, significantly differences exist in the weight average molecular weight and the ring opening degree of uronic acid).

Biological Assay

Below, the prepared products were tested from the aspects of In vitro inhibition of heparanase, inhibition of cancer cell growth, inhibition of cancer cell metastasis and acute toxicity.

Experimental Example 1: Test of In Vitro Inhibition of Heparanase

According to the method for determining the inhibitory activity against heparanase (heparitinase) in vitro in CN105744940A, the in vitro inhibitory activity against heparanase of the products prepared in this application was tested. The results are shown in the table below.

| Sample No. | Inhibitory activity against heparanase ($IC_{50}$, ng/mL) |
|---|---|
| H0242 | 17.3 |
| H0232 | 16.9 |
| H1011 | 24.3 |
| H7103 | 15.0 |
| H8261 | 20.7 |
| H8073 | 15.0 |
| H9252 | 15.2 |
| H0123 | 14.5 |
| H1301 | 13.7 |
| H1302 | 11.6 |

Experimental Example 2: Test of Inhibition of MM.1S Cell Growth

MM.1S cells were cultured in a suspension in vitro. The culture was performed with RPMI 1640 medium supplemented with 10% heat-inactivated fetal bovine serum, at 37° C. and with 5% $CO_2$. Passage cultivation was performed three times a week. When the cells were in the exponential growth phase, the cells were collected, counted, and 100 µL of a cell suspension containing $3\times10^4$ tumor cells (the cells were suspended in RPMI 1640 medium supplemented with 10% heat-inactivated fetal bovine serum, with cell viability greater than 95%) was seeded into a 96-well plate. After the cells were cultured overnight, samples formulated with RPMI 1640 medium containing 10% heat-inactivated fetal bovine serum were added to 6 wells, such that the final concentration of the samples was 100 µg/mL. An equal volume of RPMI 1640 medium containing 10% heat-inactivated fetal bovine serum was added to another 6 wells (to determine the cell absorbance at 0 µg/mL). In addition, six medium wells (complete medium wells) were set, which were the same as the others except that they were not added with cells and samples. After culture at 37° C. with 5% $CO_2$ for 48 hours, 20 µL of CCK8 reagent was added to all wells, and incubation at 37° C. with 5% $CO_2$ was performed for 1-2 hours. The absorbance at 450 nm was determined by a microplate reader. With the absorbance of the complete medium wells as the background, and the cell absorbance at 0 µg/mL as 100%, the effect of the samples on cell growth was calculated.

Inhibition rate=(cell absorbance at 0 µg/mL the absorbance of a sample well)/(cell absorbance at 0 µg/mL the absorbance of the complete medium well)(the above values are each the average of the corresponding 6 wells)

The test results are shown in the table below.

| Sample No. | Inhibition rate of MM.1S cell growth (final drug concentration was 100 µg/mL) |
|---|---|
| H0242 | 16.99% |
| H1011 | 19.21% |
| H1015 | 21.86% |
| H7103 | 20.15% |
| H8261 | 27.68% |
| H9053 | 25.13% |
| H8073 | 26.73% |
| H9252 | 22.46% |
| H0123 | 26.96% |
| H1301 | 23.84% |
| H1302 | 21.83% |

The results showed that the carboxylated derivatives of glycosaminoglycan of the present invention can significantly inhibit the growth of MM.1S cells, and the inhibitory activity is similar to that of the comparative product H1302.

Experimental Example 3: Cell Migration Test: Transwell Test (Hela Cell)

The test was performed according to Dai X Y, Yan J, Fu X et al., Aspirin inhibits cancer metastasis and angiogenesis via targeting heparanase. [J]. Clinical Cancer Research An Official Journal of the American Association for the Cancer Research, 2017, 23(20): 6267.

Hela cells were subjected to adherent culture in vitro. The culture was performed with DMEM medium supplemented with 10% heat-inactivated fetal bovine serum, at 37° C. and with 5% $CO_2$. Passage cultivation was performed three times a week. When the cells were in the exponential growth phase, the cells were collected, counted, and 100 µL of a cell suspension containing $2*10^4$ tumor cells (the cells were suspended in DMEM medium without fetal bovine serum, and the cell viability was greater than 95%) was seeded in the Transwell chamber. Outside the chamber, 600 µL of DMEM medium containing 10% heat-inactivated fetal bovine serum was added. The medium both inside and outside the chamber comprised a dissolved test sample with a final concentration of 100 µg/mL. For each sample, 3 repetitive chambers were set, and 3 additional chambers without drug were used as controls. After cultured at 37° C. with 5% $CO_2$ for 24 hours, the cells were fixed with pre-cooling 95% ethanol for 30 min. The surface inside the chamber was gently wiped with a cotton swab and unattached cells were washed away with PBS. The cells were stained with a 1% crystal violet solution, dried, and photographed to compare the number of migrated cells.

Inhibition rate of migration=(the average of the migrated cells in control wells the average of the migrated cells treated with a sample)/the average of the migrated cells in control wells The test results are shown in the table below.

| Sample No. | Inhibition rate of Hela cell migration (final drug concentration was 100 µg/mL) |
|---|---|
| H0242 | 44.78% |
| H0232 | 91.64% |
| H1011 | 66.29% |
| H1015 | 59.78% |
| H7103 | 92.93% |
| H8073 | 89.95% |
| H0123 | 84.06% |
| H1301 | 52.33% |
| H1302 | 12.17% |

The results showed that the carboxylated derivatives of glycosaminoglycan of the present application can significantly inhibit the migration of Hela cells, and have great potential in the treatment of tumors with malignant metastasis. The comparative sample H1302 had weaker activity in inhibiting migration of Hela cells.

Experimental Example 4: Animal Experiment for Lung Metastasis of In Situ 4T1 Breast Cancer 4T1 cells were cultured in a suspension in vitro. The culture was performed with RPMI 1640 medium supplemented with 10% heat-inactivated fetal bovine serum, at 37° C. and with 5% $CO_2$. Passage cultivation was performed three times a week. When the cells were in the exponential growth phase, the cells were collected, counted, and 50 µL of a cell suspension containing $1*10^5$ tumor cells (the cells were suspended in RPMI 1640 medium without fetal bovine serum) was inoculated subcutaneously on the fourth fat pad in the abdomen. The mice employed were BALB/c mice, female, 6-8 weeks old and with a body weight of 18-22 grams. According to body weights and the order of tumor inoculation, the mice were randomly grouped with 12 mice in each group. The test sample groups were administered the next day after inoculation. The administration was performed intraperitoneally twice a day at a total dose of 20 mg/kg. The negative control group was administered with a same amount of normal saline. The tumor in situ was removed on the 12th day after the tumor was inoculated, and the administration was stopped on the same day, and was continued in the above manner the day after the surgery.

Survival time of mice: each mouse was euthanized when the end point of the experiment (body weight decrease greater than 20%) was reached, and the survival time was recorded. The Kaplan-Meier survival curve was plotted.

The test results are shown in the following table and FIG. 1.

| Group | Negative control group | H1301 | H1302 | H7103 | H0123 |
|---|---|---|---|---|---|
| Median survival time (days) | 38 | 46 | 40.5 | 51 | 64 |
| Median survival time prolonged compared with the control group (%) | | 21.1% | 6.6% | 34.2% | 68% |

The results showed that the derivatives H7103, H1301 and H0123 of the present application can significantly prolong the median survival time of the model mice, especially H7103 and H0123, which can prolong the median survival time of the model mice by 34.2% and 68%, respectively. Comparative sample H1302 can slightly prolong the median survival time of the model mice, but the difference from that of the negative control group is not significant.

Experimental Example 5: Experiment for Lung Metastasis of B16 Murine Melanoma

Murine melanoma B16 cells were subjected to adherent culture in vitro. The culture was performed with RPMI 1640 medium supplemented with 10% heat-inactivated fetal bovine serum, at 37° C. and with 5% $CO_2$. Passage cultivation was performed three times a week. When the cells were in the exponential growth phase, the cells were collected, counted, and formulated as a suspension containing $2.5*10^6$ cells/mL with PBS. SPF grade healthy C57/BL6 mice with body weight of 18-20 g were selected and grouped with 8 mice per group, into a negative control group, a model group and test groups. Test samples (dissolved in normal saline at a concentration of 0.25 mg/mL) were injected into the tail veins of the mice in the test groups at a dosage of 2.5 mg/kg body weight of the mouse, and normal saline was injected into the tail veins of mice in the negative control and the model group at a dosage of 10 μL/g body weight of the mouse. The injection time was recorded sequentially. After 30 minutes, 200 μL of a cell suspension containing $5*10^5$ tumor cells (the cells were suspended in PBS, and the cell viability was greater than 90%) was injected into the tail veins of the mice in the model group and the test groups, and an equal amount of normal saline was injected into the tail veins of the mice in the control group. Animals were monitored daily and their body weight was recorded. All mice were sacrificed at the same time point from day 12 to day 14 after the cell injection. Lung tissue was taken and fixed in a Bouin solution. Tumor metastasis nodule numbers on the lung surface were counted under a stereomicroscope.

Inhibition rate of the test samples against B16 metastasis=(the median of the lung metastasis nodule numbers in the model group−the median of the lung metastasis nodule numbers in the test group)/the median of the lung metastasis nodule numbers in the model group*100%

The test results are shown in the table below.

| Sample No. | H9053 | H0242 | H9252 | H8073 | H8261 | H0123 | H7103 |
|---|---|---|---|---|---|---|---|
| Inhibition rate (%) | 25 | 18 | 37 | 90 | 85 | 93 | 92 |

The results showed that the derivatives of the present application all have significant anti-tumor metastasis activity.

Various modifications to the invention in addition to those described herein will become apparent to those skilled in the art from the foregoing description. Such modifications are intended to fall within the scope of the appended claims. Each reference, including all patents, applications, journal articles, books and any other disclosure, referred to herein is hereby incorporated by reference in its entirety.

What is claimed is:

1. A glycosaminoglycan derivative, comprising a structural unit of Formula (I), a structural unit of Formula (IV) and a structural unit of Formula (V):

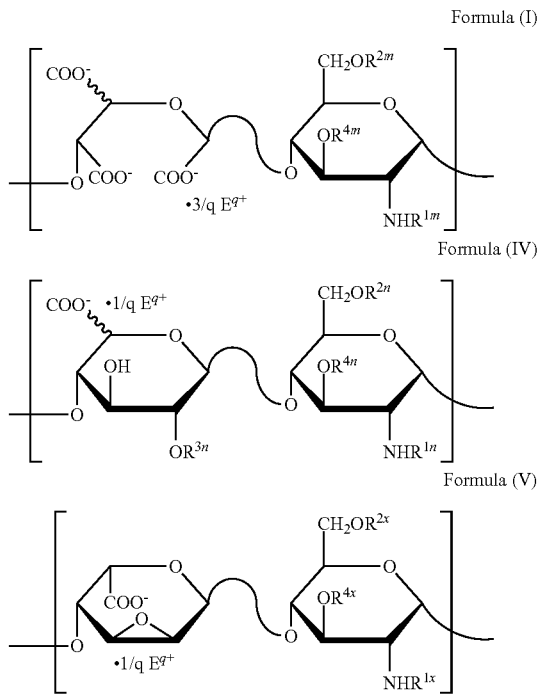

wherein:
$R^{1m}$, $R^{1n}$ and $R^{1x}$, at each occurrence, are each independently selected from the group consisting of H, $-SO_3^- \cdot (1/q\ E^{q+})$ and $-(C=O)CH_3$;
$R^{2m}$, $R^{2n}$ and $R^{2x}$, at each occurrence, are each independently selected from the group consisting of H and $-SO_3^- \cdot (1/q\ E^{q+})$;

$R^{3n}$, at each occurrence, is independently selected from the group consisting of H and —SO$_3^-$·(1/q E$^{q+}$);

$R^{4m}$, $R^{4n}$ and $R^{4x}$, at each occurrence, are each independently selected from the group consisting of H and —SO$_3^-$·(1/q E$^{q+}$);

E, at each occurrence, is independently selected from the group consisting of H, lithium, sodium, potassium, rubidium, cesium, magnesium, calcium and aluminum; and q, at each occurrence, is independently an integer of 1, 2, or 3;

wherein the glycosaminoglycan derivative has a weight average molecular weight of 7000-14000 Da; and the glycosaminoglycan derivative has a ring-opening degree of uronic acid of 25%-80%.

2. The glycosaminoglycan derivative of claim 1, further comprising a structural unit of Formula (II):

Formula (II)

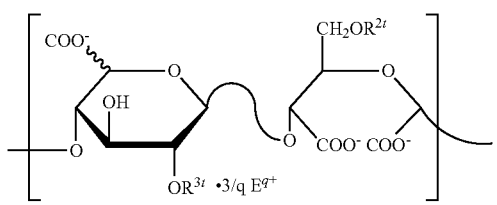

wherein:

$R^{2t}$ and $R^{3t}$, at each occurrence, are each independently selected from the group consisting of H and —SO$_3^-$·(1/q E$^{q+}$);

E, at each occurrence, is independently selected from the group consisting of H, lithium, sodium, potassium, rubidium, cesium, magnesium, calcium and aluminum; and q, at each occurrence, is independently an integer of 1, 2, or 3.

3. The glycosaminoglycan derivative of claim 1, further comprising a structural unit of Formula (III):

Formula (III)

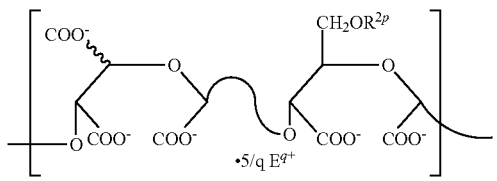

wherein:

$R^{2p}$, at each occurrence, is independently selected from the group consisting of H and —SO$_3^-$·(1/q E$^{q+}$);

E, at each occurrence, is independently selected from the group consisting of H, lithium, sodium, potassium, rubidium, cesium, magnesium, calcium and aluminum; and q, at each occurrence, is independently an integer of 1, 2, or 3.

4. The glycosaminoglycan derivative of claim 1, further comprising a structural unit of Formula (VI):

Formula (VI)

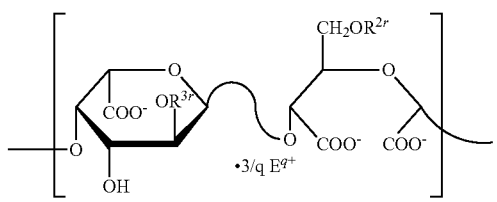

wherein:

$R^{2r}$ and $R^{3r}$, at each occurrence, are each independently selected from the group consisting of H and —SO$_3^-$·(1/q E$^{q+}$);

E, at each occurrence, is independently selected from the group consisting of H, lithium, sodium, potassium, rubidium, cesium, magnesium, calcium and aluminum; and q, at each occurrence, is independently an integer of 1, 2, or 3.

5. The glycosaminoglycan derivative of claim 1, further comprising a structural unit of Formula (VII):

Formula (VII)

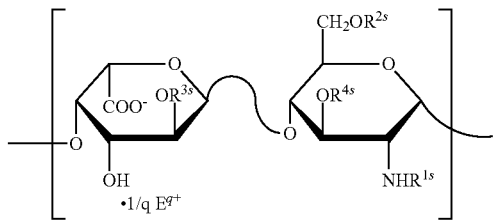

wherein:

$R^{1s}$, at each occurrence, is independently selected from the group consisting of H, H and —SO$_3^-$·(1/q E$^{q+}$) and —(C=O)CH$_3$;

$R^{2s}$, $R^{3s}$ and $R^{4s}$, at each occurrence, are each independently selected from the group consisting of H and —SO$_3^-$·(1/q E$^{q+}$);

E, at each occurrence, is independently selected from the group consisting of H, lithium, sodium, potassium, rubidium, cesium, magnesium, calcium and aluminum; and q, at each occurrence, is independently an integer of 1, 2, or 3.

6. The glycosaminoglycan derivative of claim 1, wherein the epoxy degree of uronic acid is less than 25%.

7. The glycosaminoglycan derivative of claim 1, wherein the molecular weight distribution of the glycosaminoglycan derivative is as follows:

| Molecular weight range (Da) | Proportion (% by weight) |
|---|---|
| greater than 10000 | 25-80 |
| 6000-10000 | 15-50 |
| less than 6000 | 5-50. |

8. The glycosaminoglycan derivative of claim 1, wherein the glycosaminoglycan derivative has a sulfo-carboxyl ratio of 0.80-1.65.

9. A pharmaceutical composition, comprising a prophylactically or therapeutically effective amount of the glycosaminoglycan derivative of claim 1 and a pharmaceutically acceptable carrier.

10. A method of inhibiting tumor growth and/or metastasis, comprising administering an effective amount of the glycosaminoglycan derivative of claim 1 to a subject in need thereof.

11. The method of claim 10, wherein the tumor is a solid tumor, a hematological tumor, or a soft tissue tumor.

12. The glycosaminoglycan derivative of claim 1, the glycosaminoglycan derivative has a weight average molecular weight of 8500-13000 Da.

13. The glycosaminoglycan derivative of claim 1, the glycosaminoglycan derivative has a ring-opening degree of uronic acid of 25-60%.

14. The glycosaminoglycan derivative of claim 1, wherein the molecular weight distribution of the glycosaminoglycan derivative is as follows:

| Molecular weight range (Da) | Proportion (% by weight) |
| --- | --- |
| greater than 10000 | 30-75 |
| 6000-10000 | 20-40 |
| less than 6000 | 5-30. |

15. The glycosaminoglycan derivative of claim 1, wherein the molecular weight distribution of the glycosaminoglycan derivative is as follows:

| Molecular weight range (Da) | Proportion (% by weight) |
| --- | --- |
| greater than 10000 | 30-75 |
| 6000-10000 | 20-40 |
| less than 6000 | 0-30. |

16. The glycosaminoglycan derivative of claim 1, wherein the glycosaminoglycan derivative has a sulfo-carboxyl ratio of 1.0-1.4.

17. The method of claim 11, wherein the solid tumor is breast cancer, pancreatic cancer, bladder cancer, prostate cancer, colon cancer, gastric cancer or lung cancer.

* * * * *